United States Patent
Tang et al.

(10) Patent No.: US 10,143,446 B2
(45) Date of Patent: Dec. 4, 2018

(54) METHOD OF REMOVE BLACKGROUND NOISE IN SHORT PULSE EXCITATION OF ARFI

(71) Applicant: GE MEDICAL SYSTEMS GLOBAL TECHNOLOGY COMPANY, LLC, Waukesha, WI (US)

(72) Inventors: Lu Tang, WuXi (CN); Xiaodong Han, Shanghai (CN); Gang Cheng, Shanghai (CN); Liang Shen, WuXi (CN)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 501 days.

(21) Appl. No.: 14/135,660

(22) Filed: Dec. 20, 2013

(65) Prior Publication Data

US 2014/0187951 A1  Jul. 3, 2014

(30) Foreign Application Priority Data

Dec. 31, 2012 (CN) .......................... 2012 1 0593023

(51) Int. Cl.
| | |
|---|---|
| *A61B 8/00* | (2006.01) |
| *A61B 8/08* | (2006.01) |
| *A61B 8/14* | (2006.01) |
| *G01S 7/52* | (2006.01) |

(52) U.S. Cl.
CPC .............. *A61B 8/5276* (2013.01); *A61B 8/14* (2013.01); *A61B 8/485* (2013.01); *G01S 7/52036* (2013.01); *G01S 7/52042* (2013.01); *G01S 7/52077* (2013.01)

(58) Field of Classification Search
None
See application file for complete search history.

(56) References Cited

U.S. PATENT DOCUMENTS

| | | | |
|---|---|---|---|
| 2009/0163811 A1 | 6/2009 | Fukumoto et al. | |
| 2010/0069751 A1* | 3/2010 | Hazard | A61B 5/415 600/438 |
| 2010/0286520 A1* | 11/2010 | Hazard | A61B 8/06 600/439 |
| 2011/0004100 A1* | 1/2011 | Iimura | A61B 8/0833 600/443 |
| 2012/0065507 A1* | 3/2012 | Brunke | A61B 8/12 600/442 |

(Continued)

FOREIGN PATENT DOCUMENTS

CN             101431942 A        5/2009

OTHER PUBLICATIONS

Chinese Office Action issued in connection with corresponding CN Application No. 201210593023.9 dated Aug. 2, 2017.

*Primary Examiner* — Amelie R Gillman

(57) ABSTRACT

A method for eliminating background noises in shear waves and the respective ultrasonic imaging system, the method includes: transmitting a push pulse along a push pulse vector; transmitting a first group of focus track pulses at a first group of a plurality of locations far away from the push pulse vector; receiving a first group of focus echo signals in response to the first group of focus track pulses; and processing the first group of focus echo signals to determine a first group of tissue displacement information varying with time.

16 Claims, 3 Drawing Sheets

(56) References Cited

U.S. PATENT DOCUMENTS

2012/0123262 A1* 5/2012 Xie ................. A61B 5/0048
 600/438
2013/0296698 A1* 11/2013 Fraser ............... A61B 8/4488
 600/438

* cited by examiner

METHOD OF REMOVE BLACKGROUND NOISE IN SHORT PULSE EXCITATION OF ARFI

BACKGROUND OF THE INVENTION

Embodiments of the present invention relate generally to the field of ultrasonic detection, and more particularly to a method and device for eliminating background noises in shear waves and an ultrasonic imaging system comprising the device.

Ultrasonic detection is a common detecting means in the modern medical field.

When sound waves are transmitted in a heterogeneous medium, an acoustic radiation force is produced. The acoustic radiation force can characterize bio-mechanical elasticity of tissues, which arouses interests in research on the fields of material science and medical diagnosis.

Over a long time period, one of the objectives for diagnostic imaging is precise characterization of tissues. Clinicians wish to obtain diagnostic regions of human body organs, and employ an imaging system to identify features of the tissues in the images. Ideally, clinicians expect an imaging system to identify whether a pathological state is malignant or benign. Although more efforts remain to be made to fulfill the above objective, diagnostic imaging can still reveal clues concerning the composition of tissues to clinicians. One of the technologies related to the field is elasticity imaging for use in measuring elasticity or hardness degree of tissues in a human body. For example, a highly hard breast tumor or lump may be malignant, whereas a relatively soft and more flexible lump may be benign. Owing to the relevancy between the hardness degree of a lump and its malignancy or benignancy, elasticity imaging offers clinicians another evidence useful for conducting diagnosis and working out relevant treatment solutions.

One solution is to measure shear waves. When compression on a certain point in a human body is released, the lower-strata tissues are compressed downwards and then rebound upwards during release of the compression force. Meanwhile, the tissues under the compression force link to the surrounding tissues in so continuous a way that the uncompressed tissues located at the side direction of the force vector will also make a response to the upward and downward movement of the compressed tissues. This dimple effect in the side direction is also referred to as shear waves, which serve as a response made by the surrounding tissues to the downward compression force. Further, it has been determined that the force required to push the tissues downwards can be produced by radiation pressure from ultrasonic pulses, and moreover, ultrasounds can be used to receive, perceive and measure tissue movement induced by the shear waves. The shear wave velocity is determined by mechanical properties of the local tissues. The shear waves pass through the soft tissues at a certain speed, and pass through the hard tissues at a higher speed. By measuring velocity of the shear waves at a certain point in the body, information concerning properties of the relevant tissues can be obtained, such as shear elasticity modulus, Young's modulus and dynamic shear viscosity of the tissues. The shear waves transmitted in the side direction are transmitted slowly, usually at several meters per second or even less, such that the shear waves can easily be detected, but the shear waves will quickly attenuate in a distance of several centimeters or less. Since it is allowed to repeat a same "push pulse" for each measurement, shear wave technology aids in objectively quantifying tissue properties by means of ultrasounds. In addition, the shear wave velocity is independent from the push pulse strength, thereby lessening dependency of measurement on users.

Acoustic Radiation Force Imaging (ARFI) adopts focus ultrasounds to bring radiation forces to little tissue volume. Then, conventional ultrasounds are used to track shear wave displacement of tissues, and elasticity of the tissues is calculated via an ultrasound-based relevant method. Images from the ARFI method provide mechanical impulse response information of the tissues. With respect to B mode (black-white mode), the ARFI method can improve the contrast ratio, especially when it is applied to lungs and chests. When tissues undergo pathological changes, the elasticity may change markedly. Much clinical research demonstrates that information about elasticity nature of tissues is essential to diagnosis and treatment of cancers. ARFI image, complementary to B mode image, is a method useful for characterizing mechanical characteristics of tissues.

Nevertheless, ARFI also has its own weaknesses. Its main weakness lies in that the amplitude of shear waves is extremely low and is only around 10 μm such that AFRI is sensitive to such noises as system electronic noises and a patient's movement or the like, particularly to cardiac movement or respiratory movement, which will affect estimation over the shear wave displacement. In the prior art, a solution to the aforesaid problem is to increase wave beam transmission voltage or its duration. Nonetheless, the solution will remarkably increase sound output power, even to an extent of exceeding the limitations imposed by Food and Drug Administration (FDA).

The objective of embodiments of the present invention is just to address the above problem.

BRIEF DESCRIPTION OF THE INVENTION

To the end as stated above, embodiments of the present invention provide a method for eliminating background noises in shear waves, which comprises: transmitting a push pulse along a push pulse vector; transmitting a first group of focus track pulses at a first group of a plurality of locations far away from the push pulse vector; receiving a first group of focus echo signals in response to the first group of focus track pulses; and processing the first group of focus echo signals to determine a first group of tissue displacement information varying with time.

Embodiments of the present invention further provide an ultrasonic imaging system, comprising an ultrasonic probe which can: transmit a push pulse along a push pulse vector; transmit a first group of focus track pulses at a first group of a plurality of locations far away from the push pulse vector; receive a first group of focus echo signals in response to the first group of focus track pulses, the ultrasonic imaging system processing the first group of focus echo signals to determine a first group of tissue displacement information varying with time.

Embodiments of the present invention can be applied to the ARFI ultrasonic system. According to this invention, background noises contained in shear waves can be eliminated, and the duration and voltage of the push pulses can be reduced.

BRIEF DESCRIPTION OF THE DRAWINGS

These and other objects and features of embodiments of the present invention will become better understood when the following detailed description is read with reference to the accompanying drawings, wherein.

Like characters represent same or like parts throughout the drawings.

DETAILED DESCRIPTION OF THE DRAWINGS

The following embodiments of the present invention are further explained on the basis of the drawings and embodiments.

Definitions to the selected terms used herein are given, including various examples and/or forms of components which fall into the range or scope of the terms and may be used to realize embodiments of the present invention. The examples are not limiting. These definitions may include both singular and plural forms of the terms.

References to "one embodiment", "embodiments", "one example", "examples", etc. show that the embodiment(s) or example(s) described hereinabove may include special features, structures, properties, nature, elements or limits. Nonetheless, not all embodiments or examples definitely embrace special features, structures, properties, nature, elements or limits. Besides, repeated use of the phrase "in one embodiment" may mean but not necessarily referring to a same embodiment.

For the sake of conciseness, the following description leaves out some technical features well known to persons skilled in the art.

Figure 1A:
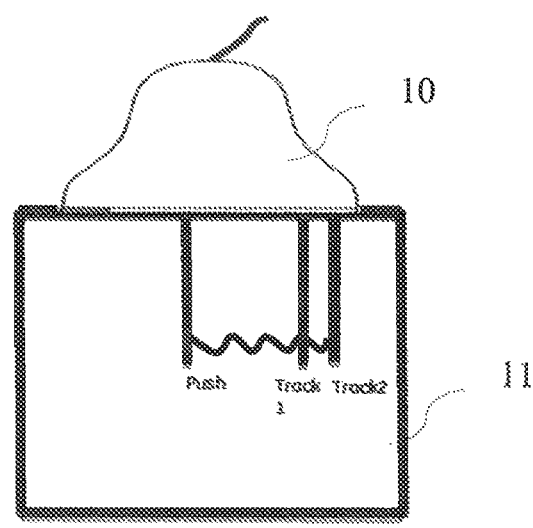
FIG. 1A and FIG. 1B are schematic diagrams showing the principle of embodiments of the present invention.
Figure 1B:
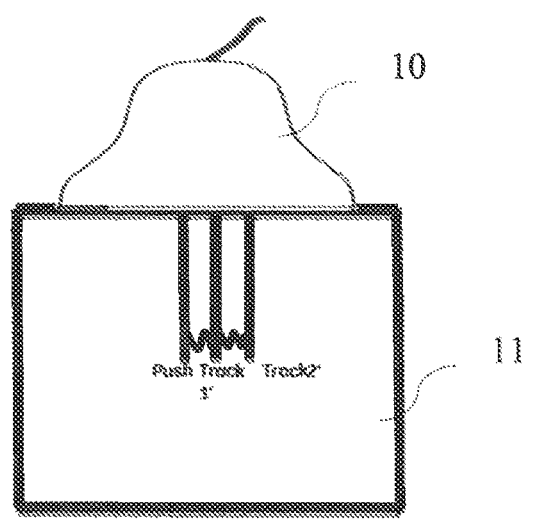

FIG. 1A and FIG. 1B schematically illustrate the principle of embodiments of the present invention. In FIG. 1A and FIG. 1B, label 10 represents an ultrasonic probe, label 11 a patient's body or a mock body, Push a push pulse, Track1 and Track2 a group of track pulses, and Track1' and Track2' another group of track pulses.

An ultrasonic probe is employed to transmit one or more push pulses to the tissues, such that ultrasonic extrusion is carried out on the tissues along the direction of the push pulse vector.

In the traditional ARFI images, push pulses are similar to color Doppler pulses. Push pulses should be long enough to generate shear waves in the tissues. The push pulses are followed by a series of track pulses which are similar to conventional B pulses. In the prior art, the track pulses are always adjacent the push pulses.

According to embodiments of the present invention, the track pulse pairs are provided with two different locations. One location is as illustrated by Track1 and Track2 in FIG. 1A. Therein, the track pulses Track1 and Track2 are located far away from the push pulse Push so as to capture noises from the tissues. The shear waves in the tissues will attenuate quickly, and thus, the shear waves have attenuated in the location of Track1 and Track2, i.e., there are no shear waves except noises therein.

The other location is identical to that in the prior art, and is as illustrated by Track1' and Track2' in FIG. 1B so as to collect the shear waves including noises.

Lastly, signals in the first location are subtracted from those in the second location to arrive at the shear waves excluding noises. In this way, the impact of noises in the tissues may be eliminated.

Figure 2:
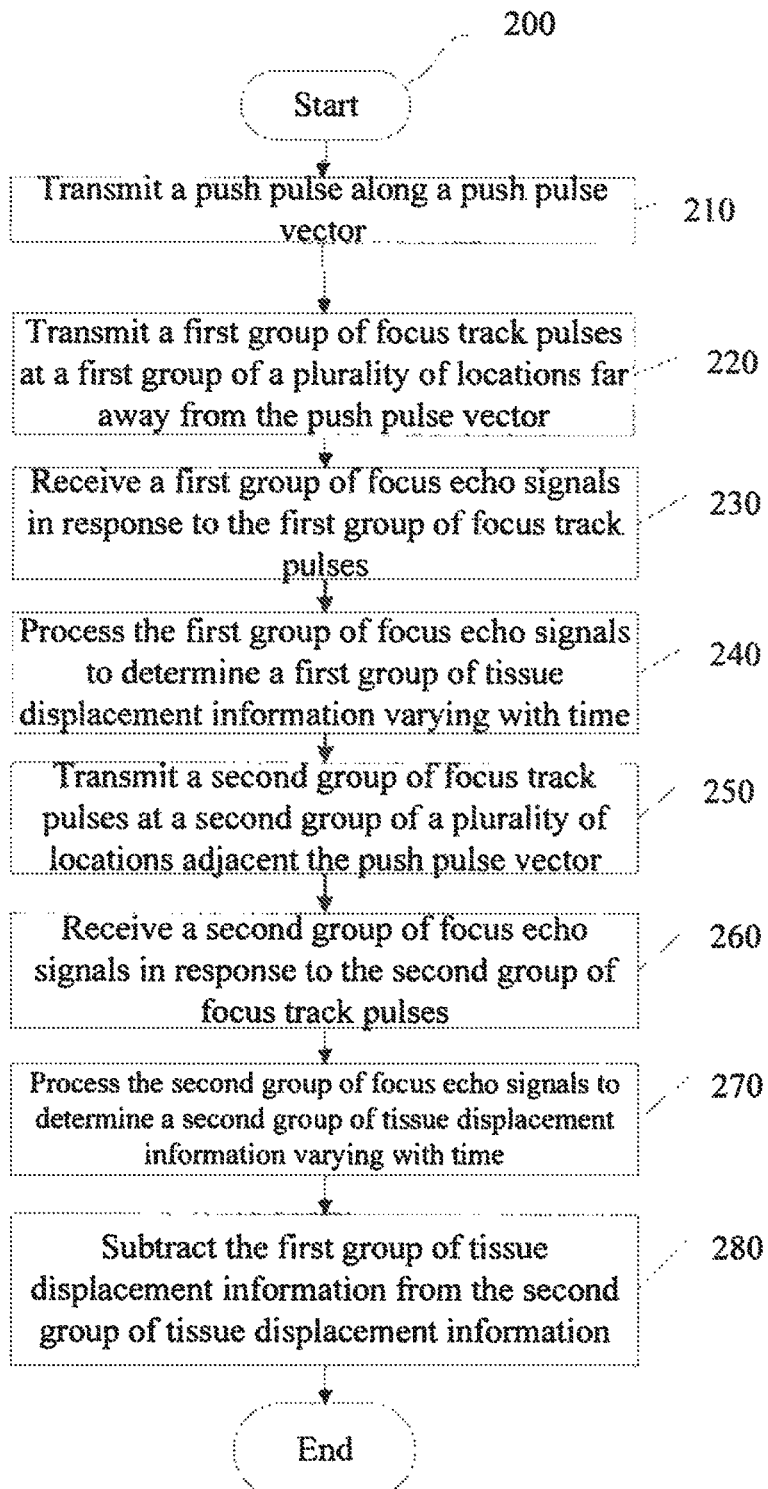
FIG. 2 is a schematic diagram showing a method for eliminating background noises in shear waves according to one embodiment of the present invention.

FIG. 2 schematically illustrates a method 200 for eliminating background noises in shear waves according to one embodiment of the present invention.

According to one embodiment of the present invention, the method 200 may include Steps 210-240.

In Step 210, a push pulse is transmitted along a push pulse vector. According to an embodiment of the present invention, a longer beam of push pulse is transmitted firstly in one frame. Upon excitation by the pulse, horizontally transmitted shear waves will occur to focus tissues.

In Step 220, a first group of focus track pulses are transmitted at a first group of a plurality of locations far away from the push pulse vector. The first group of focus track pulses may correspond to Track1 and Track2 in FIG. 1A. According to an embodiment of the present invention, a plurality of track pulses Track1 and Track2 may be transmitted alternately in turn at the location of the two wave beams Track1 and Track2, wherein the time alternation for transmitting Track1 and Track2 is given and known and the physical distance between Track1 and Track2 is given and known.

In Step 230, a first group of focus echo signals in response to the first group of focus track pulses is received. For example, each track pulse vector may be repeatedly sampled in a manner of time interleaving; accordingly, when each track pulse vector location experiences a shift resulting from the shear waves, the shift can be detected by interrelating the successively inquired echo data coming from the vector. When the shear waves move along a side direction away from the push pulse vector, positioning of the track pulses may also shift along a side direction so as to track the transmission of the shear waves.

In Step 240, the first group of focus echo signals is processed so as to determine a first group of tissue displacement information varying with time. As the first group of focus track pulses is positioned far away from the push pulse, the shear waves have attenuated. The first group of tissue displacement information includes displacement caused by background noises in the tissues, but does not include displacement caused by transmission of the shear waves.

According to another embodiment of the present invention, the method 200 may also include Steps 250-280.

In Step 250, a second group of focus track pulses are transmitted at a second group of a plurality of locations adjacent the push pulse vector. The second group of focus track pulses may correspond to Track1' and Track2' in FIG. 1B. According to an embodiment of the present invention, a plurality of track pulses Track1' and Track2' may be transmitted alternately in turn at the location of the two wave beams Track1' and Track2', wherein the time alternation for transmitting Track1' and Track2' is given and known and the physical distance between Track1' and Track2' is given and known.

In Step 260, a second group of focus echo signals in response to the second group of focus track pulses is received.

In Step 270, the second group of focus echo signals is processed so as to determine a second group of tissue displacement information varying with time. The second group of tissue displacement information includes both displacement caused by transmission of the shear waves and displacement caused by background noises in the tissues.

The background noises come from, for instance, the patient's cardiac movement or respiratory movement.

In Step 280, the first group of tissue displacement information is subtracted from the second group of tissue displacement information to obtain a subtracted group of tissue displacement information. The subtracted group of tissue displacement information merely includes the tissue displacement caused by the shear waves, thereby eliminating the background noises in the shear wave signals.

According to one embodiment of the present invention, the number of locations in the first group of the plurality of locations is equal to that of locations in the second group of the plurality of locations.

According to one embodiment of the present invention, as illustrated in FIG. 1A and FIG. 1B, the number of locations in each of the first group of the plurality of locations and the second group of the plurality of locations is 2.

According to one embodiment of the present invention, the number of locations in the first group of the plurality of locations is equal to that of locations in the second group of the plurality of locations and each is greater than 2. In this embodiment, the tissue displacement information which different locations in each group of locations correspond to can be firstly averaged such that the number of tissue displacement information included in each group of tissue displacement information is 2. For example, the first group of locations consists of 3 locations corresponding to track pulses Track1, Track2 and Track3 respectively; and the second group of locations consists of 3 locations corresponding to track pulses Track1', Track2' and Track3' respectively. Then, the tissue displacement information which Track1 and Track2 correspond to can be averaged to reach Track12; and the tissue displacement information which Track2 and Track3 correspond to can be averaged to reach Track23. Accordingly, a group of tissue displacement information Track12 and Track23 including displacement caused by background noises in the tissue, but not including displacement caused by transmission of the shear waves, can be obtained shear waves and the noises can be obtained. Subsequently, the tissue displacement information which Track1' and Track2' correspond to can be averaged to reach Track1'2'; and the tissue displacement information which Track2' and Track3' correspond to can be averaged to reach Track2'3'. Accordingly, a group of tissue displacement information Track1'2' and Track2'3' including both displacement caused by background noises in the tissue and displacement caused by transmission of the shear waves can be obtained, Lastly, the former group of tissue displacement information Track12 and Track23 is subtracted from the latter group of tissue displacement information Track1'2' and Track2'3', thereby leading to a group of tissue displacement information only including the shear waves. It shall be noted that relevant averaging manners are not confined to the above manner, but can be any averaging manners known in the art or to be developed in the future.

According to one embodiment of the present invention, the number of locations in the first group of the plurality of locations is not equal to that of locations in the second group of the plurality of locations. In this embodiment, the group of tissue displacement information concerning a greater number of locations can be firstly averaged, thereby rendering the numbers of two tissue displacement information equal to each other.

According to one embodiment of the present invention, shear wave velocity values can be calculated according to the subtracted group of tissue displacement information. For example, data from a repeatedly sampled track pulse vector can be processed so as to find out the time where the shear waves trigger peak value displacement in each point of the track pulse vector, which is realized by interrelating successive displacement measuring results, through curve fitting or interpolation. Analysis of the time where peak value displacement occurs in points of adjacent sampled vectors will bring about measuring results of the velocity of the shear waves corresponding to particular vector locations.

Figure 3:
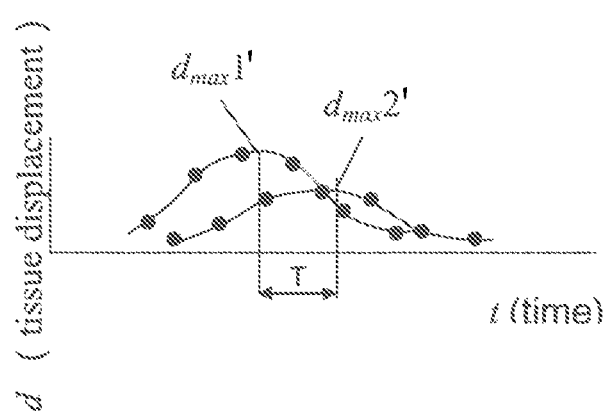
FIG. 3 is a schematic diagram illustrating the principle of calculating shear wave velocity values according to tissue displacement information.

Referring to FIG. 3, FIG. 3 schematically illustrates the principle of calculating shear wave velocity values according to the tissue displacement information.

For example, displacement of the tissues varying with time at the location of Track1' can be figured out by way of post-processing algorithm, which displacement results from the transmission of the shear waves. Likewise, displacement of the tissues varying with time at the location of Track2' can be figured out. A time difference T between a maximum value $d_{max}1'$ of displacement in the location of Track1' and a maximum value $d_{max}2'$ of displacement in the location of Track2' can be taken as a time period required for transmission of the shear waves from the location of Track1' to the location of Track 2', and further, transmission velocity of the shear waves in the tissues concerned can be figured out. To be specific, shear wave velocity=$(d_{max}1'-d_{max}2')/T$.

According to one embodiment of the present invention, a Young's modulus can be calculated according to the shear wave velocity values. Stated in another way, velocity variation shows different degrees of hardness or elasticity in the tissues. Since there is a relation between the transmission velocity of the shear waves and the Young's modulus of the tissues as described below, the Yong's Modulus can be derived, i.e., $$\text{shear wave velocity} = \sqrt{\frac{E}{2(1+v)\rho}}$$

wherein E is a Young's modulus, $\rho$ is density of the tissues and v is Poisson ratio.

According to one embodiment of the present invention, the background noises come from the patient's cardiac movement or respiratory movement.

As the shear waves attenuate very quickly, generally, it is impossible to collect shear wave data of the whole image field by using a single push pulse vector. Therefore, it is necessary to repeat the above process in another location of the tissues so as to collect shear wave velocity measuring results in another area of the tissues. The process will be repeated before the shear wave in the whole expected image field has been collected.

Embodiments of the present invention also provide an ultrasonic imaging system, comprising the following ultrasonic probe.

The ultrasonic probe can transmit a push pulse along a push pulse vector. According to an embodiment of the present invention, a longer beam of push pulse is transmitted firstly in one frame. Upon excitation by the pulse, horizontally transmitted shear waves will occur to focus tissues.

The ultrasonic probe can also transmit a first group of focus track pulses at a first group of a plurality of locations far away from the push pulse vector. The first group of focus track pulses can correspond to Track1 and Track2 in FIG. 1A. According to an embodiment of the present invention, a plurality of track pulses Track1 and Track2 can be transmitted alternately in turn at the location of the two wave beams Track1 and Track2, wherein the time alternation for transmitting Track1 and Track2 is given and known and the physical distance between Track1 and Track2 is given and known.

The ultrasonic probe can also receive a first group of focus echo signals in response to the first group of focus track pulses. For example, each track pulse vector can be repeatedly sampled in a manner of time interleaving; accordingly, when each track pulse vector location experiences a shift resulting from the shear waves, the shift can be detected by interrelating the successively inquired echo data coming from the vector. When the shear waves move along a side direction away from the push pulse vector, positioning of the track pulses can also shift along a side direction so as to track the transmission of the shear waves.

The ultrasonic imaging system of embodiments of the present invention can process the first group of focus echo signals so as to determine a first group of tissue displacement information varying with time. As the first group of focus track pulses is positioned far away from the push pulse, the shear waves have attenuated. The first group of tissue displacement information includes displacement caused by the background noises in the tissues, but does not include displacement caused by the transmission of the shear waves.

The ultrasonic probe can also transmit a second group of focus track pulses at a second group of a plurality of locations adjacent the push pulse vector. The second group of focus track pulses can correspond to Track1' and Track2' in FIG. 1B. According to an embodiment of the present invention, a plurality of track pulses Track1' and Track2' can be transmitted alternately in turn at the location of the two wave beams Track1' and Track2', wherein the time alternation for transmitting Track1' and Track2' is given and known and the physical distance between Track1' and Track2' is given and known.

The ultrasonic probe can also receive a second group of focus echo signals in response to the second group of focus track pulses.

The ultrasonic imaging system of embodiments of the present invention can also process the second group of focus echo signals so as to determine a second group of tissue displacement information varying with time. The second group of tissue displacement information includes both displacement caused by the transmission of the shear waves and displacement caused by the background noises in the tissues. These background noises come from, for instance, the patient's cardiac movement or respiratory movement.

The ultrasonic imaging system of embodiments of the present invention can also subtract the first group of tissue displacement information from the second group of tissue displacement information to obtain a subtracted group of tissue displacement information. The subtracted group of tissue displacement information merely includes the tissue displacement caused by the shear waves, thereby eliminating the background noises in the shear wave signals.

According to one embodiment of the present invention, the number of locations in the first group of the plurality of locations is equal to that of locations in the second group of the plurality of locations.

According to one embodiment of the present invention, as illustrated in FIG. 1A and FIG. 1B, the number of locations in each of the first group of the plurality of locations and the second group of the plurality of locations is 2.

According to one embodiment of the present invention, the number of locations in each of the first and second groups of the plurality of locations is greater than 2. In this embodiment, tissue displacement information which different locations in each group of locations correspond to can be first averaged such that the number of tissue displacement information included in each group of tissue displacement information is 2. For example, the first group of locations consists of 3 locations corresponding to track pulses Track1, Track2 and Track3 respectively; and the second group of locations consists of 3 locations corresponding to track pulses Track1', Track2' and Track3' respectively. Then, the tissue displacement information which Track1 and Track2 correspond to can be averaged to reach Track12; and the tissue displacement information which Track2 and Track3 correspond to can be averaged to reach Track23. Accordingly, a group of tissue displacement information Track12 and Track23 including displacement caused by background noises in the tissue, but not including displacement caused by transmission of the shear waves, can be obtained. Subsequently, the tissue displacement information which Track1' and Track2' correspond to can be averaged to reach Track1'2'; and the tissue displacement information which Track2' and Track3' correspond to can be averaged to reach Track2'3'. Accordingly, a group of tissue displacement information Track1'2' and Track2'3' including both displacement caused by background noises in the tissue and displacement caused by transmission of the shear waves can be obtained. Lastly, the former group of tissue displacement information Track12 and Track 23 is subtracted from the latter group of tissue displacement information Track1'2' and Track2'3', thereby leading to a group of tissue displacement information only including the shear waves. It shall be noted that relevant averaging manners are not confined to the above manner, but can be any averaging manners known in the art or to be developed in the future.

According to one embodiment of the present invention, the number of locations in the first group of the plurality of locations is not equal to that of locations in the second group of the plurality of locations. In this embodiment, the group of tissue displacement information concerning a greater number of locations can be firstly averaged, thereby rendering the numbers of two tissue displacement information equal to each other.

According to one embodiment of the present invention, the ultrasonic imaging system can also calculate shear wave velocity values according to the subtracted group of tissue displacement information. For example, data from a repeatedly sampled track pulse vector can be processed so as to find out the time where the shear waves trigger peak value displacement in each point of the track pulse vector, which is realized by interrelating the successive displacement measuring results, through curve fitting or interpolation. Analysis of the time where peak value displacement occurs in points of adjacent sampled vectors will bring about measuring results of the velocity of shear waves corresponding to particular vector locations.

According to one embodiment of the present invention, the ultrasonic imaging system can also calculate a Young's modulus according to the shear wave velocity values. Stated in another way, velocity variation shows different degrees of hardness or elasticity in the tissues. Since there is a relation between the transmission velocity of the shear waves and the Young's modulus of the tissues as described below, the Young's Modulus can be derived, i.e., $$\text{shear wave velocity} = \sqrt{\frac{E}{2(1+v)\rho}}$$

wherein E is a Young's modulus, ρ is density of the tissues and v is Poisson ratio.

According to one embodiment of the present invention, background noises come from the patient's cardiac movement or respiratory movement.

The technical solution of embodiments of the present invention can be applied to the ARFI ultrasonic system. According to embodiments of the present invention, background noises contained in shear waves can be eliminated. Hence, embodiments of the present invention differ from the prior art in no need to increase the duration or transmission voltage of wave beams.

According to embodiments of the present invention, duration of push pulses can be reduced, thereby remarkably decreasing sound output power. Thus, embodiments of the present invention can not only put the sound output power within the limitations set by FDA, but also is more reliable from patients' perspective. The duration and voltage of push pulses can be reduced.

Embodiments of the present invention have better effects than the complicated filter adopted in the post-period processing.

It is to be noted that the embodiments described above are simply exemplary and non-limiting. Moreover, under the circumstance of not deviating from the range of the claims attached, persons skilled in the art can devise more alternative embodiments. The wording "comprise" used herein means not excluding other components and steps than those recited in the claims or the description. Besides, the number of the components involved herein can be one or more. The reference numbers in the parentheses in the claims are not considered as any limitations to the claims.

What is claimed is:

1. A method for operating an ultrasonic imaging system to eliminate background noises in shear waves, the method comprising:
   transmitting a push pulse along a push pulse vector;
   transmitting a first group of focus track pulses at a first plurality of locations having different distances in the same direction far away from the push pulse vector to capture background noise, wherein the track pulses are transmitted alternately in turn along the different distances in the same direction, wherein the plurality of locations comprises a first location, a second location, and a third location;
   receiving a first group of interleaved focus echo signals in response to the first group of focus track pulses;
   processing the first group of focus echo signals to determine a first group of tissue displacement information varying with time, where the first group of tissue displacement information comprises: first tissue displacement information corresponding to the first location; second tissue displacement information corresponding to the second location, and third tissue displacement information corresponding to the third location;
   averaging the first tissue displacement information with the second tissue displacement information to generate first average tissue displacement information;
   averaging the second tissue displacement information with the third tissue displacement information to generate second average tissue displacement information;
   transmitting a second group of focus track pulses alternately in turn at a second plurality of locations, adjacent the push pulse vector, the second plurality of locations comprising a fourth location and a fifth location;
   receiving a second group of focus echo signals in response to the second group of focus track pulses;
   processing the second group of focus echo signals to determine a second group of tissue displacement information varying with time, where the second group of tissue displacement information comprises fourth tissue displacement information associated with the fourth location and fifth tissue displacement information associated with the fifth location;
   subtracting the first average tissue displacement information from one of the fourth tissue displacement information and a third average tissue displacement information, calculated using the fourth tissue displacement information, to generate first displacement information excluding the background noise; and
   subtracting the second average tissue displacement information from one of the fifth tissue displacement information and a fourth average tissue displacement information, calculated using the fifth tissue displacement information, to generate second displacement information excluding the background noise.

2. The method according to claim 1, wherein the second plurality of locations further comprises a sixth location, and wherein the second group of tissue displacement information further comprises sixth tissue displacement information associated with the sixth location.

3. The method according to claim 2, further comprising calculating the third average tissue displacement information by averaging the fourth tissue displacement information with the fifth tissue displacement information, and wherein the first displacement information excluding the background noise is generated by subtracting the first average tissue displacement information from the third average tissue displacement information.

4. The method according to claim 1, wherein the second plurality of locations consists of the fourth location and the fifth location.

5. The method according to claim 4, wherein the first displacement information excluding the background noise is generated by subtracting the first average tissue displacement information from the fourth tissue displacement information.

6. The method according to claim 5, wherein the second displacement information excluding the background noise is generated by subtracting the second average tissue displacement information from the fifth tissue displacement information.

7. The method according to claim 1, further comprising generating the fourth average tissue displacement information by averaging the fifth tissue displacement information with the sixth tissue displacement information, and wherein generating the second displacement information excluding the background noise comprises subtracting the second average tissue displacement information from the fourth average tissue displacement information.

8. The method according to claim 1, further comprising calculating a shear wave velocity using the first displacement information excluding the background noise and the second displacement information excluding the background noise.

9. An ultrasonic imaging system, comprising:
   an ultrasonic probe configured to:
      transmit a push pulse along a push pulse vector;
      transmitting a first group of focus track pulses at a first plurality of locations having different distances in the same direction far away from the push pulse vector to capture background noise, wherein the track pulses are transmitted alternately in turn along the different distances in the same direction, wherein the plurality of locations comprises a first location, a second location, and a third location;

receive a first group of interleaved focus echo signals in response to the first group of focus track pulses; and a processor configured to:

process the first group of focus echo signals to determine a first group of tissue displacement information varying with time, where the first group of tissue displacement information comprises: first tissue displacement information corresponding to the first location; second tissue displacement information corresponding to the second location, and third tissue displacement information corresponding to the third location;

average the first tissue displacement information with the second tissue displacement information to generate first average tissue displacement information;

average the second tissue displacement information with the third tissue displacement information to generate second average tissue displacement information;

transmit a second group of focus track pulses alternately in turn at a second plurality of locations adjacent the push pulse vector, the second plurality of locations comprising a fourth location and a fifth location;

receive a second group of focus echo signals in response to the second group of focus track pulses;

process the second group of focus echo signals to determine a second group of tissue displacement information varying with time, where the second group of tissue displacement information comprises fourth tissue displacement information associated with the fourth location and fifth tissue displacement information associated with the fifth location;

subtract the first average tissue displacement information from one of the fourth tissue displacement information and a third average tissue displacement information, calculated using the fourth tissue displacement information, to generate first displacement information excluding the background noise; and subtract the second average tissue displacement information from one of the fifth tissue displacement information and a fourth average tissue displacement information, calculated using the fifth tissue displacement information, to generate second displacement information excluding the background noise.

10. The ultrasonic imaging system according to claim 9, wherein the second plurality of locations consists of the fourth location and the fifth location, and wherein the processor is configured to generate the first tissue displacement information excluding the background noise by subtracting the first average tissue displacement information from the fourth tissue displacement information.

11. The ultrasonic imaging system according to claim 10, wherein the processor is configured to generated the second displacement information excluding the background noise by subtracting the second average tissue displacement information from the fifth tissue displacement information.

12. The ultrasonic imaging system according to claim 9, wherein the second group of tissue displacement information comprises sixth tissue displacement information from a sixth location, wherein the processor is configured to calculate the third average tissue displacement information by averaging the fourth tissue displacement information with the fifth tissue displacement information, and wherein the processor is configured to generate the first displacement information excluding the background noise by subtracting the first average tissue displacement information from the third average tissue displacement information.

13. The ultrasonic imaging system according to claim 12, wherein the processor is configured to generate fourth average tissue displacement information by averaging the fifth tissue displacement information with the sixth tissue displacement information, and wherein the processor is configured to generate the second displacement information excluding the background noise by subtracting the second average tissue displacement information from the fourth average tissue displacement information.

14. The ultrasonic imaging system according to claim 9, wherein the processor is further configured to calculate a shear wave velocity using the first displacement information excluding the background noise and the second displacement information excluding the background noise.

15. The method according to claim 14, wherein the processor is configured to calculate a Young's modulus according to the shear wave velocity.

16. The ultrasonic imaging system according to claim 9, wherein the background noise comprises cardiac movement or respiratory movement.

* * * * *